United States Patent [19]

Boden et al.

[11] Patent Number: 4,900,718
[45] Date of Patent: Feb. 13, 1990

[54] 3-(2-BORNYLOXY)-2-METHYL-1-PROPANOL AND PERFUMERY USES THEREOF

[75] Inventors: Richard M. Boden, Ocean; William J. Fylak, Allenhurst; Joseph A. Mc Ghie, South Orange; Jordi Castells, Westfield, all of N.J.

[73] Assignee: International Flavors & Fragrances Inc., New York, N.Y.

[21] Appl. No.: 386,146

[22] Filed: Jul. 28, 1989

[51] Int. Cl.$^4$ .............................................. A61K 7/46
[52] U.S. Cl. ................................. 512/19; 252/174.11; 252/8.6; 568/665
[58] Field of Search ...................... 568/665; 512/4, 19; 252/174.11, 8.6

[56] References Cited

U.S. PATENT DOCUMENTS 3,354,225 11/1967 Kane .................................... 568/665
4,698,180 10/1987 Pavlin .............................. 252/522 R
4,715,981 12/1987 Fujioka et al. .................. 252/174.11

Primary Examiner—James H. Reamer
Attorney, Agent, or Firm—Arthur L. Liberman

[57] ABSTRACT

Described is 3-(2-bornyloxy)-2-methyl-1-propanol defined according to the chemical structure:

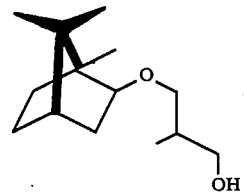

and organoleptic uses thereof in augmenting or enhancing the aroma of perfume compositions, colognes and perfumed articles including but not limited to solid or liquid anionic, cationic, nonionic or zwitterionic detergents, fabric softener compositions, fabric softener articles, perfumed polymers, cosmetic powders and hair preparations.

8 Claims, 4 Drawing Sheets

IR SPECTRUM FOR EXAMPLE I.

3-(2-BORNYLOXY)-2-METHYL-1-PROPANOL AND PERFUMERY USES THEREOF

BACKGROUND OF THE INVENTION

The instant invention provides 3-(2-bornyloxy)-2-methyl-1-propanol having the structure:

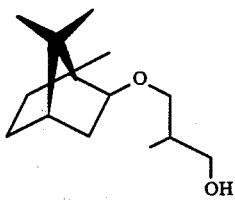

and perfumery uses thereof.

Inexpensive, long-lasting and intense dry, woody, cedarwood, tobacco-like, ambery and patchouli aroma nuances with woody, musty and mushroom topnotes are highly desirable in the art of perfumery. Many of the natural materials which provide such fragrances and contribute such desired nuances to perfumery compositions as well as perfumed articles including solid or liquid anionic, cationic, nonionic or zwitterionic detergents, perfumed polymers, fabric softener compositions, fabric softener articles, hair preparations, cosmetic powders and the like are high in cost, vary in quality from one batch to another and/or are generally subject to the usual variations of natural products.

U.S. Pat. No. 3,354,225 (Kane) issued on Nov. 21, 1967 (Class 568, Subclass 665) discloses the cedarwood aroma of the compound having the structure:

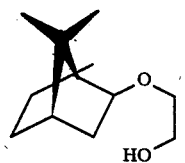

commercially available under the name "Arbinol". The compound having the structure:

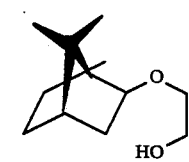

has aroma qualities different in kind and has a substantivity and strength substantially less than 3-(2-bornyloxy)-2-methyl-1-propanol of our invention having the structure:

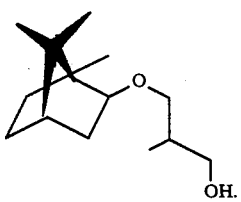

U.S. Pat. No. 4,698,180 (Pavlin) issued on Oct. 6, 1987 (Class 252, Subclass 522) discloses the woody aroma of the compound having the structure:

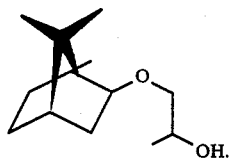

The compound having the structure:

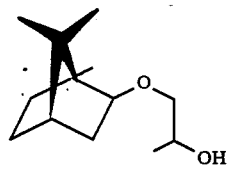

has aroma qualities different in kind and has a substantivity and strength substantially less than the compound having the structure:

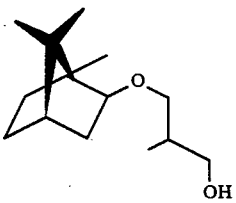

of our invention.

U.S. Pat. No. 4,715,981 issued on Dec. 29, 1987 (Class 252, Subclass 174.11) discloses the cedarwood, patchouli and incense aroma profile of the mixture of compounds including compounds having the structures:

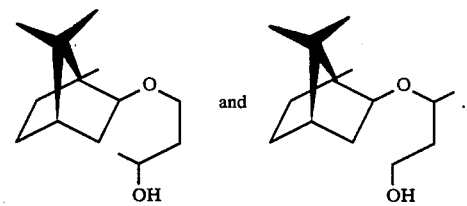

The mixture of compounds including compounds having the structures:

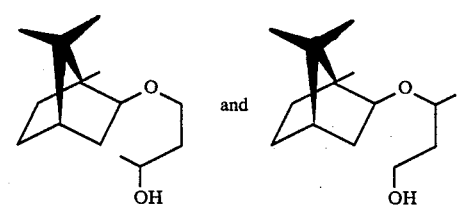

disclosed in U.S. Pat. No. 4,715,981 has aroma qualities different in kind and has a substantivity and strength substantially less than the 3-(2-bornyloxy)-2-methyl-1-propanol of our invention having the structure:

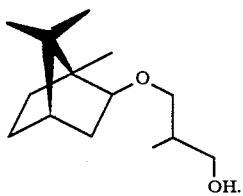

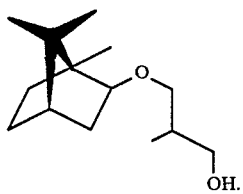

Figure 2:
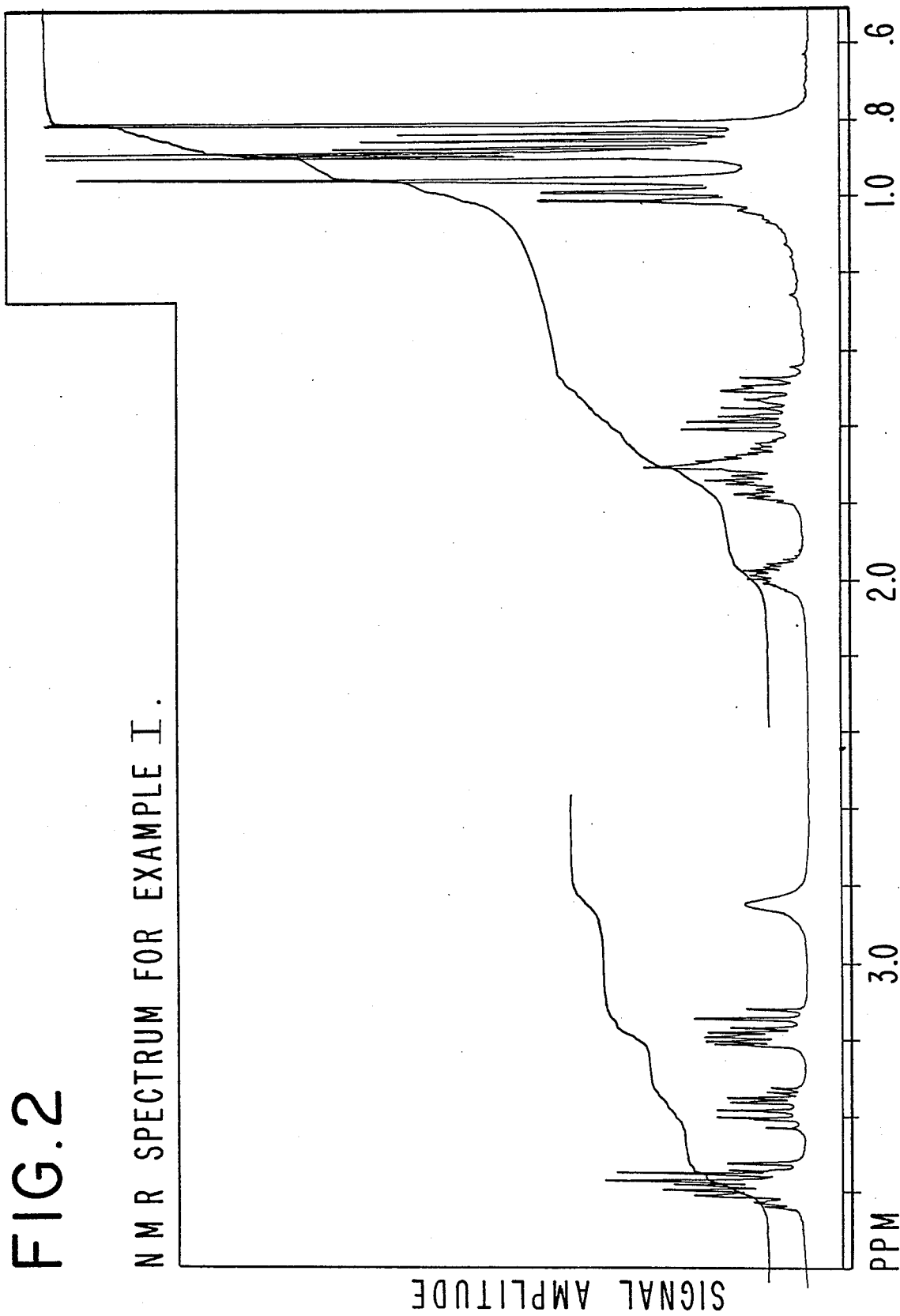

FIG. 2 is the NMR spectrum for the compound having the structure:

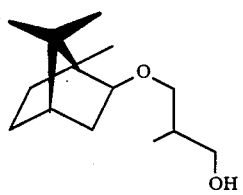

prepared according to Example I.

Figure 3:
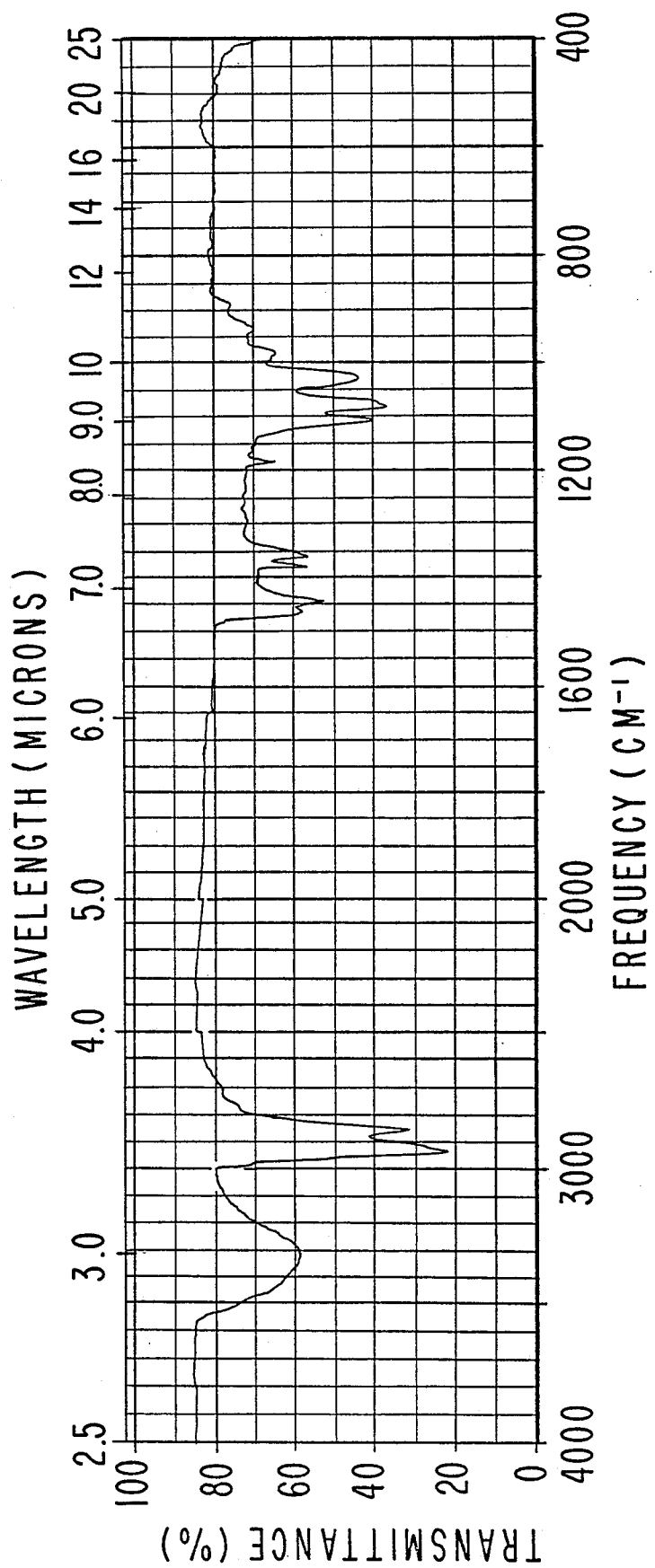

FIG. 3 is the infra-red spectrum for the compound having the structure:

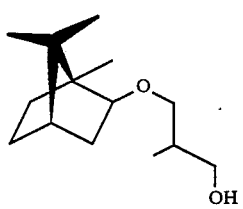

prepared according to Example I.

Figure 4:
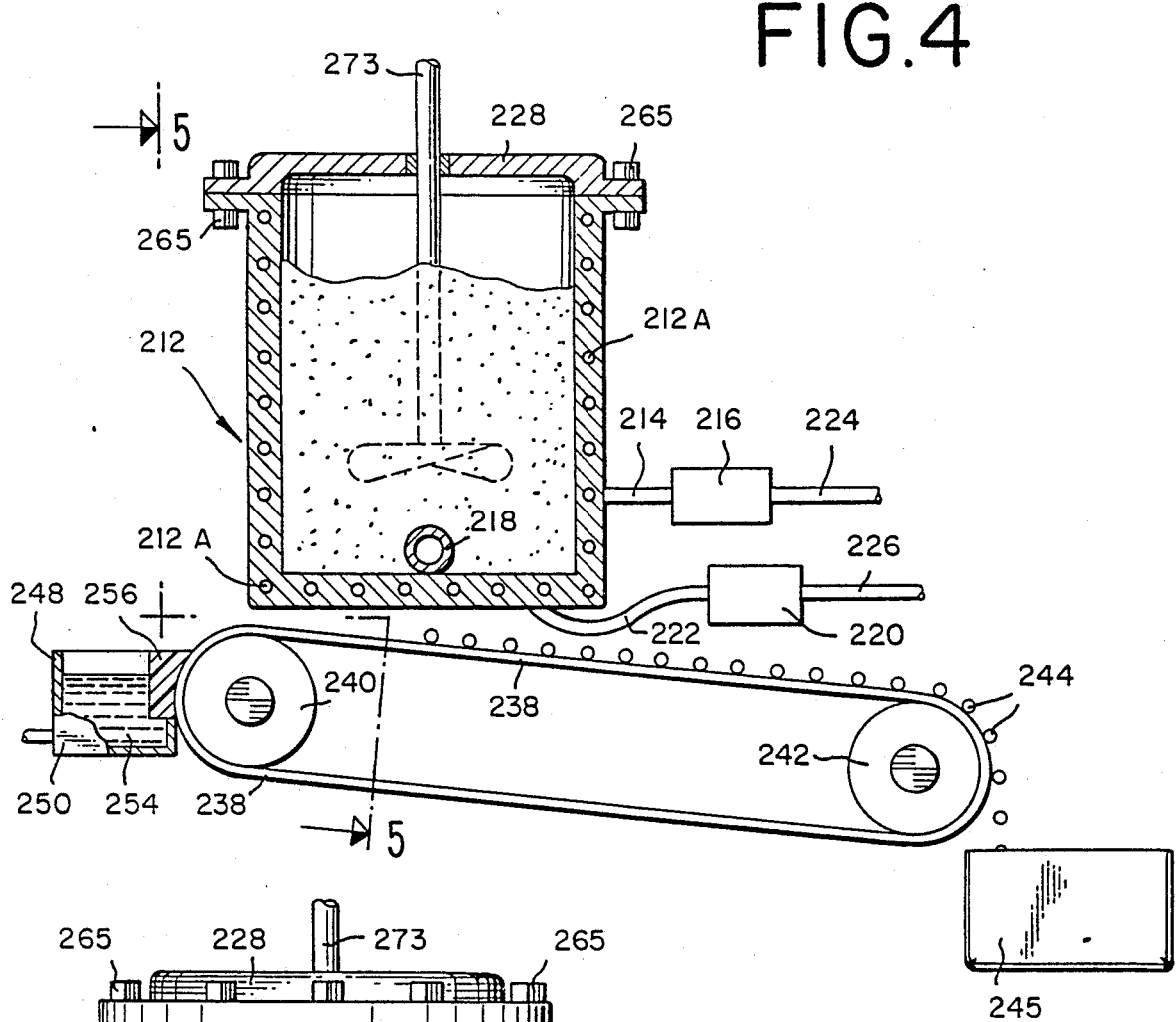

FIG. 4 represents a cut-away side elevation view of apparatus used in forming perfumed polymers which contain imbedded therein the 3-(2-bornyloxy)-2-methyl-1-propanol of our invention.

Figure 5:
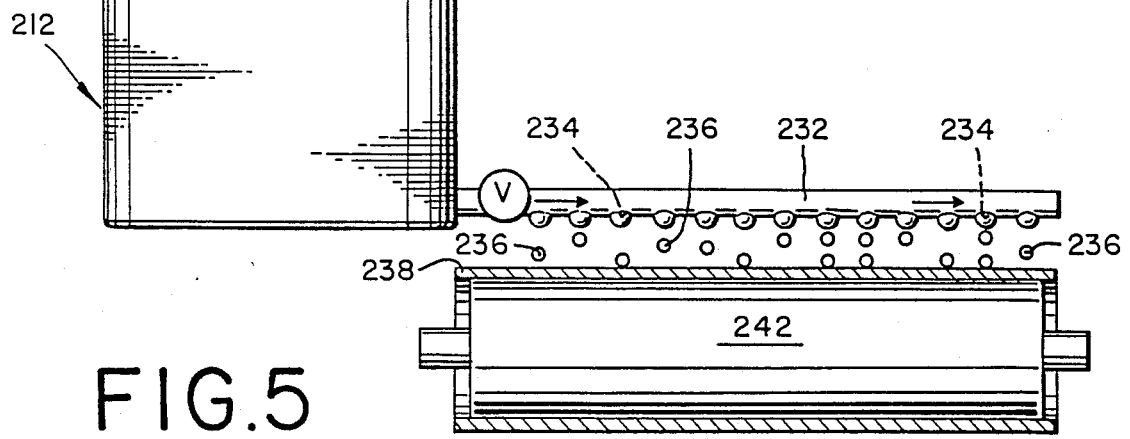

FIG. 5 is a front view of the apparatus of FIG. 4 looking in the direction of the arrows.

DETAILED DESCRIPTION OF THE DRAWINGS

Figure 1:
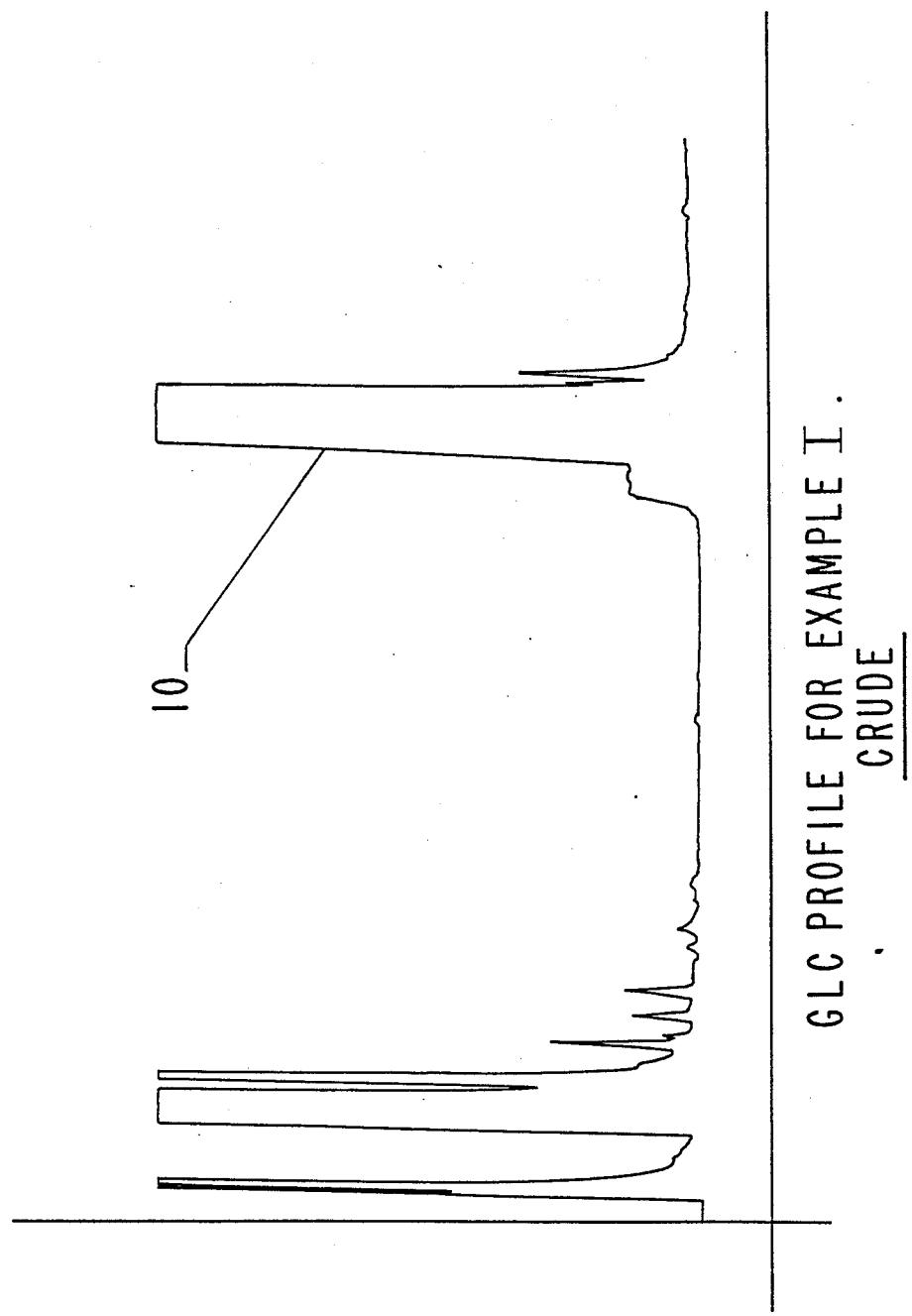
FIG. 1 is the GLC profile for the reaction product of Example I containing the compound having the structure.

FIG. 1 is the GLC profile of the crude reaction product of Example I containing the compound having the structure:

The peak indicated by reference numeral 10 is the peak for the compound having the structure:

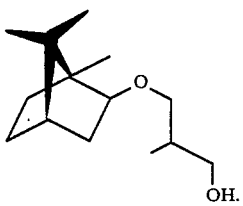

Referring to FIGS. 4 and 5 there is provided a process for forming scented polymer elements (wherein the polymer may be a thermoplastic polymer such as low density polyethylene or polypropylene or copolymers of ethylene and vinyl acetate or mixtures of polymers and copolymers such as copolymers of ethylene and vinyl acetate and polyethylene) such as pellets useful in the formation of plastic particles useful in fabricating certain articles which may be perfumed. The process comprises heating the polymer or mixture of polymers to the melting point of said polymer or mixture of polymers, e.g., 250° C. in the case of low density polyethylene. The lowermost portion of the container 212 is maintained at a slightly lower temperature and the material in the container is taken off at such location for delivery through the conduit. Thus, referring to FIGS. 4 and 5, in particular, the apparatus used in producing such elements comprises a device for forming the polymer containing perfume, e.g., polyethylene or polyethylene-polyvinyl acetate or mixtures of same or polypropylene, which comprises a vat or container 212 into which the polymer taken alone or in admixture with other copolymers and the perfuming substance which is a mixture of the 3-(2-bornyloxy)-2-methyl-1-propanol of our invention and other compatible perfumes (if desired) is placed. The container is closed by means of an air-tight lid 228 and clamped to the container by bolts 265. A stirrer 273 traverses the lid or cover 228 in air-tight manner and is rotatable in a suitable manner. A surrounding cylinder 212 having heating coils 212A which are supplied with electric current through cables 214 and 222 from rheostats or controls 216 or 220 is operated to maintain the temperature inside the container 212 such that the polymer in the container will be maintained in the molten or liquid state. It has been found advantageous to employ polymers at such a temperature that the viscosity will be in the range of 90-100 sayboldt seconds. The heater 218 is operated to maintain the upper portion of the container 212 within a temperature range of, for example, 220°-270° C. in the case of low density polyethylene. The bottom portion of the container 212 is heated by means of heating coils 212A regulated through the control 220 and the control 216 connected thereto through connecting wires 222 and 214 respectively to maintain the lower portion of the container 212 within a temperature range of 220°–270° C.

Thus, the polymer or mixture of polymers added to the container 212 is heated from 10–12 hours, whereafter the perfume composition or perfume material which contains the 3-(2-bornyloxy)-2-methyl-1-propanol of our invention is quickly added to the melt. Generally, about 10–45% by weight of the resulting mixture of the perfumery substance containing the 3-(2-bornyloxy)-2-methyl-1-propanol of our invention is added to the polymer.

After the perfume material is added to the container 212, the mixture is stirred for a few minutes, for example, 5–15 minutes and maintained within the temperature ranges indicated previously by the heating coil 212A. The controls 216 and 220 are connected through cables 224 and 226 to a suitable supply of electric current for supplying the power for heating purposes.

Thereafter, the valve "V" is opened permitting the mass to flow outwardly through conduit 232 having a multiplicity of orifices 234 adjacent to the lower side thereof. The outer end of the conduit 232 is closed so that the liquid polymer in intimate admixture with the 3-(2-bornyloxy)-2-methyl-1-propanol of our invention taken alone or taken further together with other perfume substances will continuously drop through the orifices 234 downwardly from the conduit 232. During this time, the temperature of the polymer intimately admixed with the perfumery substance in the container 212 is accurately controlled so that a temperature in the range of from about 240°–250° C., for example, (in the case of low density polyethylene) will exist in the conduit 232. The regulation of the temperature through the controls 216 and 220 is essential in order to insure temperature balance to provide for the continuous dripping or dropping of molten polymer intimately admixed with the perfume substance (containing 3-(2-bornyloxy)-2-methyl-1-propanol and if desired other materials compatible with 3-(2-bornyloxy)-2-methyl-1-propanol) through the orifices 234 at a rate which will insure the formation of droplets 236 which will fall downwardly onto a moving conveyor belt 238 caused to run between conveyor wheels 240 and 242 beneath the conduit 232.

When the droplets 236 fall onto the conveyor 238, they form pellets 244 which harden almost instantaneously and fall off the end of the conveyor 238 into a container 250 which is advantageously filled with water 254 or some other suitable cooling liquid 254 to insure the rapid cooling of each of the pellets 244. The pellets are then collected from the container 250 and utilized for the formation of other functional products, e.g., garbage bags and the like.

THE INVENTION

The present invention provides 3-(2-bornyloxy)-2-methyl-1-propanol defined according to the structure:

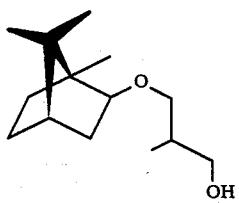

prepared according to the process of reacting camphene having the structure:

with 1,3-dihydroxy-2-methyl propane according to the reaction:

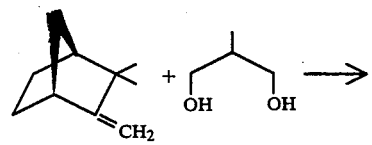

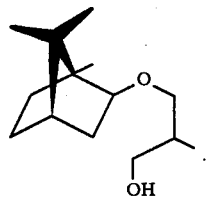

The resulting 3-(2-bornyloxy)-2-methyl-1-propanol produced according to the above-mentioned process is capable of augmenting or enhancing the aroma and/or taste of consumable materials including but not limited to perfume compositions, colognes and perfumed articles (including but not limited to soaps, anionic, cationic, nonionic or zwitterionic detergents, fabric softener compositions, fabric softener articles, optical brightener compositions, perfumed polymers, hair preparations and the like) thus fulfilling a need in the field of perfumery as well as detergent, cologne, fabric softener and cosmetic manufacture.

The reaction, to wit:

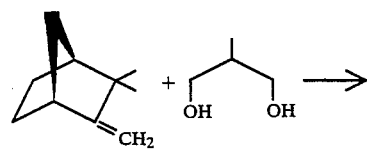

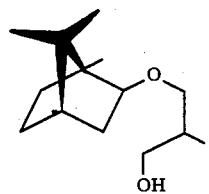

is carried out in the presence of a protonic acid catalyst or a Lewis acid catalyst.

Thus, when the reaction takes place in the presence of a catalyst which is a Lewis acid, for example, borontrifluoride etherate, zinc chloride, stannic chloride, diethyl aluminum chloride, ethyl dialuminum chloride or the like, the reaction temperature may range from about 60° C. up to about 100° C. at pressures in the range of from about one atmosphere up to about ten atmospheres. Preferably, the reaction when using a Lewis acid catalyst takes place at 70° C. at atmospheric pressure and at reflux conditions. The reaction time may vary from about two hours up to about twenty hours depending upon temperature of the reaction. Higher temperatures of reaction give rise to lower times of reaction and lower temperatures of reaction give rise to high times of reaction but a better overall yield of 3-(2-bornyloxy)-2-methyl-1-propanol. The mole ratio of 1,3-dihydroxy-2-methyl propane to camphene may vary from about 1:2 up to about 3:1 with a mole ratio of diol:camphene of about 2:1 being preferred. At the end of the reaction the reaction mass is neutralized and the reaction product having the structure:

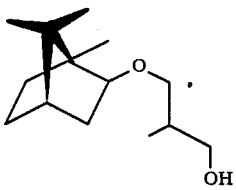

is purified for organoleptic uses as by means of fractional distillation.

When using a protonic acid catalyst, such protonic acids as concentrated sulfuric acid (e.g., 92% aqueous sulfuric acid), concentrated phosphoric acid, paratoluene sulphonic acid and methane sulphonic acid as well as xylene sulphonic acid may be used. When the reaction, to wit:

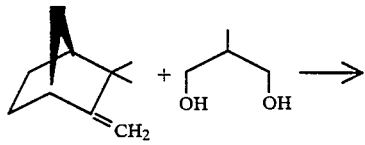

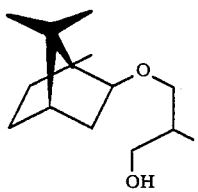

takes place in the presence of a protonic acid, the mole ratio of 1,3-dihydroxy-2-methyl propane:camphene may vary from about 3:1 down to about 1:1 with a preferred mole ratio of about 1.5:1 of 1,3-dihydroxy-2-methyl propane:camphene. The amount of protonic acid in the reaction mass based on moles camphene reactant may vary from about 0.5% up to about 3% of the camphene reactant with a preferred mole ratio of about 1% of the protonic acid, e.g., concentrated sulfuric acid. The reaction temperature may vary between about 120° C. and about 160° C. with a preferred reaction temperature of from about 135°-150° C. The reaction time may vary from about one hour up to about ten hours. Higher temperatures of reaction give rise to lower times of reaction and lower temperatures of reaction give rise to high times of reaction but a better overall yield. At the end of the reaction, the reaction mass is neutralized and the reaction product defined according to the structure:

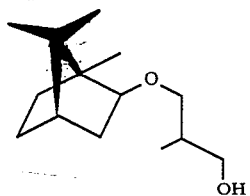

is purified for organoleptic uses by means of fractional distillation.

The 3-(2-bornyloxy)-2-methyl-1-propanol of our invention and one or more auxiliary perfume ingredients, including, for example, alcohols other than that of our invention; aldehydes; ketones; terpenic hydrocarbons; nitriles; esters; lactones; ethers other than the ether of our invention; natural essential oils; and synthetic essential oils may be admixed so that the combined odors of the individual components produce a pleasant and desired fragrance, particularly and preferably in the amber, cedarwood and patchouli area.

Such perfume compositions usually contain (a) the main note or the "bouquet" or foundation stone of the composition; (b) modifiers which round off and accompany the main note; (c) fixatives which include odorous substances which lend a particular note to the perfume throughout all stages of evaporation and substances which retard evaporation; and (d) topnotes which are usually low boiling, fresh smelling materials.

In perfume compositions, it is the individual components which contribute to their particular olfactory characteristics, however, the overall sensory effect of the perfume compositions will be at least the sum total of the effects of each of the ingredients. Thus, the 3-(2-bornyloxy)-2-methyl-1-propanol of our invention can be used to alter, modify, or enhance the aroma characteristics of a perfume composition, for example, by utilizing or moderating the olfactory reaction contributed by another ingredient in the composition.

The amount of the 3-(2-bornyloxy)-2-methyl-1-propanol of our invention which will be effective in perfume compositions as well as in perfumed articles (e.g., anionic, cationic, nonionic or zwitterionic solid or liquid detergents, soaps, fabric softener compositions, drier-added fabric softener articles, optical brightener compositions, perfumed polymers and textile sizing agents) and colognes depends on many factors, including the other ingredients, their amounts and the effects which are desired. It has been found that perfume compositions con- taining as little as 0.05% of the 3-(2-bornyloxy)-2-methyl-1-propanol of our invention prepared in accordance with the process set forth, supra, and less than 50% of the 3-(2-bornyloxy)-2-methyl-1-propanol of our invention or even less (e.g., 0.005%) can be used to impart, augment or enhance dry, woody, cedarwood, tobacco-like, ambery and patchouli aromas with woody, musty and mushroom topnotes to soaps, cosmetics, solid or liquid anionic, cationic, nonionic or zwitterionic detergents, fabric softener compositions, fabric softener articles, optical brightener compositions, textile sizing compositions, perfumed polymers or other products. The amount employed can range up to 70% of the fragrance components and will depend on considerations of cost, nature of the end product, the effect desired on the finished product and the particular fragrance sought.

The 3-(2-bornyloxy)-2-methyl-1-propanol of our invention is useful (taken alone or with other ingredients) in perfume compositions as (an) olfactory component(s) in detergents and soaps, space odorants and deodorants, perfumes, colognes, toilet water, bath preparations, such as creams, deodorants, hand lotions and sun screens; powders, such as talcs, dusting powders, face powders and perfumed polymers and articles of manufacture produced from said perfumed polymers, e.g., garbage bags, children's toys and the like. When used as (an) olfactory component(s) as little as 0.2% of the 3-(2-bornyloxy)-2-methyl-1-propanol of our invention will suffice to impart, augment or enhance dry, woody, cedarwood, tobacco-like, ambery and patchouli aromas with woody, musty and mushroom topnotes to spicy, amber and patchouli formulations. Generally, no more than 6% of the 3-(2-bornyloxy)-2-methyl-1-propanol of our invention based on the ultimate end product are required in the perfumed article composition. Accordingly, the range of 3-(2-bornyloxy)-2-methyl-1-propanol of our invention in the perfumed article is from about 0.2% by weight of 3-(2-bornyloxy)-2-methyl-1-propanol up to about 6% by weight of 3-(2-bornyloxy)-2-methyl-1-propanol based on the total weight of perfumed articles.

In addition, the perfume or fragrance composition of our invention can contain a vehicle for the 3-(2-bornyloxy)-2-methyl-1-propanol of our invention. The vehicle can be a liquid, such as a non-toxic alcohol, e.g., ethyl alcohol, a non-toxic glycol, e.g., propylene glycol or the like. The carrier can also be an absorbent solid, such as a gum (e.g., gum arabic or xanthan gum) or components for encapsulating the composition (such as gelatin as by coacervation or such as, urea formaldehyde prepolymer forming a capsule shell around a liquid perfumed center.

Our invention also relates to the utilization of controlled release technology for the controlled release of perfumes into gaseous environments from polymers such as mixtures of epsilon polycaprolactone polymers and polyethylene according to the disclosure of U.S. Pat. No. 4,715,981 at columns 10, 11 and 12, the specification for which is incorporated by reference herein.

The following Example I serves to provide a process for preparing the 3-(2-bornyloxy)-2-methyl-1-propanol of our invention. The examples following Example I are illustrative of the organoleptic utilities of the 3-(2-bornyloxy)-2-methyl-1-propanol of our invention.

All parts and percentages given herein are by weight unless otherwise specified.

EXAMPLE I

PREPARATION OF 3-(2-BORNYLOXY)-2-METHYL-1-PROPANOL

Reaction:

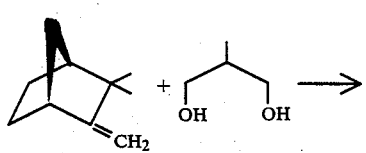

-continued

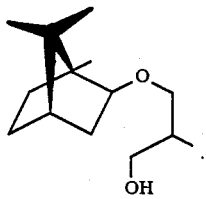

Into a 3 liter reaction flask equipped with stirrer, thermometer, reflux condenser and heating mantle is placed 864.5 grams (5 moles) of 80% camphene and 900 grams (10 moles) of 2-methyl-1,3-propanediol.

Over a period of five minutes 15 cc of borontrifluoride is added to the reaction mass.

The reaction mass is then heated to 70° C. for a period of 60 minutes.

An additional 5 cc of borontrifluoride is then added and heating is continued for an additional one hour.

The heating mantle is removed and the reaction mass is cooled and washed with one 1,000 cc portion of water. The reaction mass is then fractionally distilled on a 12" Goodloe column yielding the following fractions:

| Fraction No. | Vapor Temp. (°C.) | Liquid Temp. (°C.) | Vacuum mm/Hg. Pressure | Weight of Fraction |
|---|---|---|---|---|
| 1 | 75/100 | 120/130 | 1.5/1.2 | 40.0 |
| 2 | 100 | 130 | 1.2 | 41.0 |
| 3 | 100 | 130 | 1.0 | 102.0 |
| 4 | 103 | 126 | 1.0 | 61.0 |
| 5 | 101 | 130 | 1.0 | 96.0 |
| 6 | 100 | 130 | 1.0 | 98.0 |
| 7 | 100 | 130 | 1.0 | 114.0 |
| 8 | 100 | 142 | 1.0 | 104.0 |
| 9 | 100 | 150 | 1.0 | 71.0 |
| 10 | 100 | 155 | 1.0 | 50.0. |

The resulting product has a dry, woody, cedarwood, tabacco-like, ambery and patchouli aroma profile with woody, musty and mushroom topnotes.

FIG. 1 is the GLC profile for the crude reaction product containing the compound having the structure:

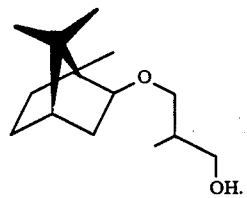

The peak indicated by reference numeral 10 is the peak for the compound having the structure:

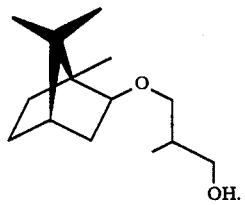

FIG. 2 is the NMR spectrum for the compound having the structure:

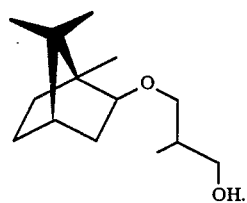

FIG. 3 is the infra-red spectrum for the compound having the structure:

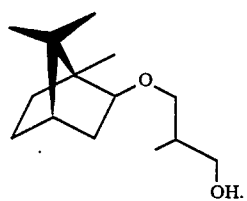

EXAMPLE II

Preparation of Pine Fragrance

| The following pine fragrance formulation is prepared: | |
|---|---|
| Ingredients | Parts by Weight |
| Isobornyl acetate | 100 |
| Camphor | 10 |
| Alpha-Terpineol | 25 |
| Fir balsam absolute | 20 |
| (50% in diethyl phthalate) | |
| Coumarin | 4 |
| Linalool | 30 |
| Fenchyl alcohol | 10 |
| Anethole | 12 |
| Lemon terpenes washed | 50 |
| Borneol | 5 |
| Galbanum oil | 5 |
| Turpentine Russian | 150 |
| Eucalyptol | 50 |
| 2,2,6-trimethyl-1-cyclohexene-1-carboxaldehyde | 12 |
| Maltol (1% in diethyl phthalate) | 15 |

| Ingredients | Parts by Weight |
|---|---|
| Compound having the structure: [structure] prepared according to Example I. | 28 |

The compound having the structure: imparts to the pine formulation an intense dry, woody, cedarwood, tobacco-like, ambery and patchouli undertone with woody, musty and mushroom topnotes. Accordingly, the perfume composition of this example can be described as "piney, with a dry, woody, cedarwood, tobacco-like, ambery and patchouli undertone with woody, musty and mushroom topnotes".

EXAMPLE III

Preparation of Cosmetic Powder Compositions

Cosmetic powder compositions are prepared by mixing in a ball mill 100 grams of talcum powder with 0.25 grams of each of the substances set forth in Table I below. Each of the cosmetic powder compositions has an excellent aroma as described in Table I below:

| Substance | Aroma Description |
|---|---|
| The compound having the structure: [structure] prepared according to Example I, bulked distillation fractions 3-10. | A dry, woody, cedarwood, tobacco-like, amber and patchouli aroma profile with woody, musty and mushroom topnotes. |
| Perfume composition of Example II. | Piney, with a dry, woody, cedarwood, tobacco-like, ambery and patchouli undertone with woody, musty and mushroom topnotes |

EXAMPLE IV

Perfumed Liquid Detergent

Concentrated liquid detergents with aromas as set forth in Table I of Example III (which detergents are prepared from Lysine salt of n-dedecyl benzene sulfonic acid as more specifically described in U.S. Pat. No. 3,948,818 issued on Apr. 6, 1976 the specification for which is incorporated by reference herein) are prepared containing each of the substances set forth in Table I of Example III, supra. They are prepared by adding and homogeneously mixing the appropriate quantity of perfumery substance as set forth in Table I of Example III in the liquid detergent. The detergents all possess aromas as set forth in Table I of Example III, the intensity increasing with greater concentrations of perfumery substance of Table I of Example III, supra.

EXAMPLE V

Preparation of a Cologne and Handkerchief Perfume

The perfume substances of Table I of Example III, supra, are incorporated into colognes at concentrations of 1.5%, 2.0%, 2.5%, 3.0% and 4.0% in 80%, 85% and 90% aqueous ethanols; and into a handkerchief perfume compositions at concentrations of 10%, 15%, 20%, 25% and 30% (in 85%, 90% and 95% aqueous ethanols). Distinct and definite aromas as set forth in Table I of Example III are imparted to the cologne and to the handkerchief perfume compositions.

EXAMPLE VI

Preparation of a Detergent Composition

A total of 100 grams of a detergent powder (a non-ionic detergent powder containing a proteolytic enzyme prepared accoding to Example I of Canadian Pat. No. 985,190 issued on Mar. 9, 1976 the disclosure of which is incorporated by reference herein) is mixed with 0.15 grams of each of the substances set forth in Table I of Example III, supra, until substantially homogeneous compositions are obtained. These compositions have excellent aromas as set forth in Table I of Example III.

EXAMPLE VII

Preparation of Soap

Each of the perfumery substances of Table I of Example III are incorporated into soap (LVU-1) at 0.1% by weight of each substance. After two weeks in the oven at 90° F. each of the soaps showed no visual effect from the heat. Each of the soaps manifested an excellent aroma as set forth in Table I of Example III, supra.

EXAMPLE VIII

Preparation of Soap Composition

One hundred grams of soap chips (IVORY ®, registered trademark of the Procter & Gamble Company of Cincinnati, Ohio) are mixed individually with one gram each of the perfumery substances of Table I of Example III, supra, until a homogeneous composition is obtained. The homogeneous composition is then treated under three atmospheres pressure at 180° C. for a period of three hours and the resulting liquid is placed into a soap mold. The resulting soap cakes, on cooling, manifest excellent aromas as set forth in Table I of Example III, supra.

EXAMPLE IX

Preparation of a Solid Detergent Composition

A detergent is prepared from the following ingredients according to Example I of Canadian Letters Patent No. 1,007,948 (the specification for which is incorporated by reference herein):

| Ingredients | Parts by Weight |
|---|---|
| "Neodol 45-II" (a $C_{14}$–$C_{15}$ alcohol ethoxylated with 11 moles of ethylene oxide) | 12 |
| Sodium carbonate | 55 |
| Sodium citrate | 20 |
| Sodium sulfate, water brighteners | q.s. |

This detergent is a "phosphate-free" detergent. A total of 100 grams of this detergent is admixed separately with 0.15 grams of each of the perfume substances of Table I of Example III, supra. The detergent samples each have excellent aromas as set forth in Table I of Example III, supra.

EXAMPLE X

Utilizing the procedure of Example I at column 15 of U.S. Pat. No. 3,632,396 (the specification for which is incorporated by reference herein), a non-woven cloth substrate useful as a drier-added fabric softening article of manufacture is prepared, wherein the substrate, the substrate coating and the outer coating and the perfuming material are as follows:

1. a water "dissolvable" paper ("Dissolvo Paper");
2. Adogen 448 (m.p. about 140° F.) as the substrate coating; and
3. an outer coating having the following formulation (m.p. about 150° F.):
   57 percent $C_{20-22}$ HAPS
   22 percent isopropyl alcohol
   20 percent antistatic agent
   1 percent of one of the perfume substances of Table I of Example III, supra.

A fabric softening composition prepared as set forth above having the above aroma characteristics as set forth in Table I of Example III, supra, essentially consists of a substrate having a weight of about 3 grams per 100 square inches, a substrate coating of about 1.85 grams per 100 square inches of substrate and an outer coating of about 1.4 grams per 100 square inches of substrate, thereby providing a total aromatized substrate and outer coating weight ratio of about 1:1 by weight of substrate. The aroma set forth in Table I of Example III is imparted in a pleasant manner to the headspace in the dryer on operation thereof, using said drier-added fabric softening non-woven fabric.

What is claimed is:

1. The 3-(2-bornyloxy)-2-methyl-1-propanol having the structure:

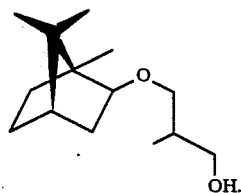

2. A process for augmenting or enhancing the aroma of a perfume, cologne or perfumed article comprising the step of intimately admixing with said perfume, cologne or perfumed article, an aroma augmenting or enhancing quantity of the 3-(2-bornyloxy)-2-methyl-1-propanol of claim 1.

3. A process for augmenting or enhancing the aroma of a solid or liquid anionic, cationic, nonionic or zwitterionic detergent comprising the step of adding to said solid or liquid anionic, cationic, nonionic or zwitterionic detergent, an aroma augmenting or enhancing quantity of 3-(2-bornyloxy)-2-methyl-1-propanol having the structure:

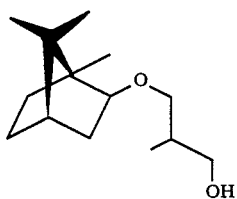

4. The process of claim 2 wherein the 3-(2-bornyloxy)-2-methyl-1-propanol having the structure:

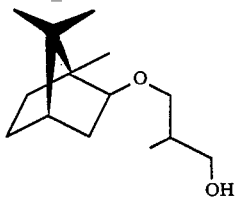

is added to a perfumed polymer.

5. A perfumed polymer comprising a polymer and intimately admixed therewith the 3-(2-bornyloxy)-2-methyl-1-propanol having the structure:

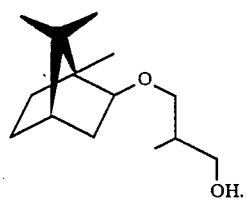

6. A perfume composition comprising a perfume base and intimately admixed therewith, an aroma augmenting or enhancing quantity of the 3-(2-bornyloxy)-2-methyl-1-propanol of claim 1.

7. A fabric softener composition or fabric softener article comprising a fabric softener composition base or fabric softener article base and intimately admixed therewith the 3-(2-bornyloxy)-2-methyl-1-propanol of claim 1.

8. A cologne comprising alcohol, water and an aroma imparting quantity of the 3-(2-bornyloxy)-2-methyl-1-propanol of claim 1.

* * * * *